US005874537A

United States Patent [19]
Kelman et al.

[11] Patent Number: 5,874,537
[45] Date of Patent: *Feb. 23, 1999

[54] METHOD FOR SEALING TISSUES WITH COLLAGEN-BASED SEALANTS

[75] Inventors: Charles D. Kelman, New York, N.Y.; Dale P. DeVore, Chelmsford, Mass.

[73] Assignee: C. R. Bard, Inc., Murray Hill, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 610,853

[22] Filed: Mar. 5, 1996

Related U.S. Application Data

[60] Continuation of Ser. No. 321,095, Oct. 7, 1994, abandoned, which is a division of Ser. No. 31,665, Mar. 15, 1993, Pat. No. 5,354,336, which is a division of Ser. No. 646,944, Jan. 29, 1991, Pat. No. 5,219,895.

[51] Int. Cl.⁶ ............................. A61K 38/17; A61F 2/16
[52] U.S. Cl. ..................... 530/356; 530/402; 530/408; 530/410; 514/21; 522/68; 623/6
[58] Field of Search ................................ 530/356, 402, 530/408, 410; 514/21; 522/68; 623/6

[56] References Cited

U.S. PATENT DOCUMENTS

| | | | |
|---|---|---|---|
| 3,438,374 | 4/1969 | Falb et al. | 606/214 |
| 3,453,222 | 7/1969 | Young | 260/8 |
| 3,515,551 | 6/1970 | Audran et al. | 96/35 |
| 4,215,200 | 7/1980 | Miyata et al. | 106/155 |
| 4,233,360 | 11/1980 | Lucky et al. | 428/310 |
| 4,264,155 | 4/1981 | Miyata | 351/160 H |
| 4,264,493 | 4/1981 | Battista | 260/117 |
| 4,349,470 | 9/1982 | Battista | 260/117 |
| 4,388,428 | 6/1983 | Kuzma et al. | 523/106 |
| 4,407,787 | 10/1983 | Sternberger | 424/28 |
| 4,427,808 | 1/1984 | Stol et al. | 524/24 |
| 4,451,568 | 5/1984 | Schneider et al | 623/66 |
| 4,452,925 | 6/1984 | Kuzma et al. | 523/106 |
| 4,453,939 | 6/1984 | Zimmerman et al. | 604/368 |
| 4,488,911 | 12/1984 | Luck et al. | 106/161 |
| 4,563,490 | 1/1986 | Stol et al. | 524/24 |
| 4,565,580 | 1/1986 | Miyata et al. | 106/124 |
| 4,581,030 | 4/1986 | Bruns et al. | 623/5 |
| 4,606,910 | 8/1986 | Sawyer | 424/28 |
| 4,650,616 | 3/1987 | Wajs | 264/2.6 |

(List continued on next page.)

FOREIGN PATENT DOCUMENTS

| | | |
|---|---|---|
| A-0 191 994 | 8/1986 | European Pat. Off. . |
| 0 244 688-A2 | 11/1987 | European Pat. Off. . |
| A-0 330 344 | 8/1989 | European Pat. Off. . |
| 466 383 A1 | 1/1992 | European Pat. Off. . |
| PCT/US97/ 08124 | of 0000 | WIPO . |
| WO 83/00339 | 2/1983 | WIPO . |
| WO92/13025 | 8/1992 | WIPO . |
| WO94/21306 | 9/1994 | WIPO . |
| WO-A-93 02639 | 2/1995 | WIPO . |
| WO96/ 03159A1 | 2/1996 | WIPO . |

OTHER PUBLICATIONS

Shimizu, et al., *Biomat., Med. Dev. Art. Org.*, 5(1):49–66 (1977).
Shimizu, et al., *Biomat., Med. Dev. Art. Org.*, 6(4):375–391 (1978).
Lloyd, et al., D.R., "biomedical and Dental Applications of Ploymers", C.G. Cobelein et al. (eds)., Plenum Press (1980), pp. 59–84.
"Collagen as a Biomaterial", Stenzel, et al., pp. 231–253 (1974).
"Polyurenthanes", Galligan, et al., J.D., Chapter 16, pp. 255–267 (1970).
"Bonding to Hard Dental Tissues", Buonocore, M.G., Chapter 15, pp. 225–254 (1970).
Surface Preparation and Various Adhesive Resins, Lee, Jr. et al., H.L., Chapter 17, pp. 269–289 (1970).
ARVO Annual Meeting Abstract Issue, Investigative Ophthalmology and Visual Science, De Toledo, et al., A.R., vol. 31 (1990), p. 317.
ARVO Annual Meeting Abstract Issue, Investigative Ophthalmology and Visual Science, De Toledo, et al., A.R., vol. 31 (1990), p. 387.
Kram, et al., H.b., *Arch Surg*, 119:1309–1311 (1984).
Scheele, et al., Surgery, 95(1):6–13 (1982).
Siedentop, et al., K.H., *Laryngoscope*, 93:1310–1313 (1983).
Epstein, et al., G.H., *Annals of Otology, Rhinology & Laryngology*, 95(1):40–45 (1986).
De Toledo, et al., ARVO Annual Meeting Abstract Issue, Investigative Opthalmalogy and Visual Science, 1556–14 (1990) Abstract.
Scott, et al., ARVO Annual Meeting Abstract Issue, Investigative Opthalmalogy and Visual Science, 431–11:30 (1990) Abstract.
Fisher, "Collagen Goes Beyond the Cosmetic", *The New York Times*, Jan. 29, 1991.
Science Watch,Fining a Natural Glue, The New York Times, 1990.
Braunwald, N., Evaluation of crosslinked gelatin as a tissue adhesive . . . , Surgery, 59:6:1024–1030, (1966).
Snyder, et al., "An improved 2, 4, 6–Trinitrobenzenesulfonic . . . ", *Analytical Biochemistry*, 64:284–288, (1975).
Aldrich Chemical Company Brochure, (1990).

*Primary Examiner*—Cecilia J. Tsang
*Assistant Examiner*—Abdel A. Mohamed
*Attorney, Agent, or Firm*—Testa, Hurwitz & Thibeault, LLP

[57] ABSTRACT

Collagen-based compositions as adhesives and sealants for medical use and preparation thereof are described. Prior to polymerization, soluble or partially fibrillar collagen monomers in solution are chemically modified with an acylating agent, sulfonating agent or a combination of the foregoing. The collagen compositions prepared accordingly can be used as medical adhesives for bonding soft tissues or be made in to a sealant film for a variety of medical uses such as wound closures and tendon wraps for preventing adhesion formation following surgery.

17 Claims, 2 Drawing Sheets

U.S. PATENT DOCUMENTS

| | | | |
|---|---|---|---|
| 4,713,446 | 12/1987 | DeVore et al. | 530/356 |
| 4,789,663 | 12/1988 | Wallace et al. | 514/21 |
| 4,837,285 | 6/1989 | Berg et al. | 530/356 |
| 4,839,345 | 6/1989 | Doi et al. | 514/21 |
| 4,950,699 | 8/1990 | Holman | 524/21 |
| 4,969,912 | 11/1990 | Kelman et al. | 623/66 |
| 5,024,742 | 6/1991 | Nesburn et al. | 204/157.68 |
| 5,067,916 | 11/1991 | Kelman et al. | 623/5 |
| 5,104,957 | 4/1992 | Kelman et al. | 527/201 |
| 5,112,350 | 5/1992 | Civevchia et al. | 606/107 |
| 5,147,514 | 9/1992 | Mechanic | 204/156.68 |
| 5,156,613 | 10/1992 | Sawyer | 606/214 |
| 5,173,295 | 12/1992 | Wehling | 424/94.67 |
| 5,190,057 | 3/1993 | Sarfarazi | 604/294 |
| 5,209,776 | 5/1993 | Bass et al. | 606/214 |
| 5,279,825 | 1/1994 | Wehling | 424/94.67 |
| 5,290,552 | 3/1994 | Sierra | 424/94.64 |
| 5,292,362 | 3/1994 | Bass et al. | 106/124 |
| 5,294,314 | 3/1994 | Nesburn et al. | 204/157.68 |
| 5,352,715 | 10/1994 | Wallace et al. | 523/115 |
| 5,354,336 | 10/1994 | Kelman et al. | 623/6 |
| 5,356,614 | 10/1994 | Sharma | 424/45 |
| 5,412,076 | 5/1995 | Gagnieu | 530/356 |
| 5,431,790 | 7/1995 | Nesburn et al. | 204/157.68 |
| 5,441,491 | 8/1995 | Verschoor et al. | 603/304 |

UV IRRADIATION

METHOD FOR SEALING TISSUES WITH COLLAGEN-BASED SEALANTS

This is a continuation of application Ser. No. 08/321,095, filed Oct. 7, 1994, now abandoned, which is a division of Ser. No. 08/031,665, filed Mar. 15, 1993, U.S. Pat. No. 5,354,336, which is a division of Ser. No. 07/646,944, filed Jan. 29, 1991, U.S. Pat. No. 5,219,895.

FIELD AND BACKGROUND OF THE INVENTION

The ability to establish bonding between biological tissues has long been a goal of biomedical researchers. Attempts to provide desired adhesion through mechanical bonding have proven to be neither convenient nor permanent (Buonocore, M., *Adhesion in Biological Systems*, R. S. Manly, ed., Academic Press, New York, 1970, Chap. 15). For this reason, much attention was devoted to developing synthetic polymers, e.g., cyanoacrylates, as biomedical adhesives. These plastic materials, however, have been observed to induce inflammatory tissue reaction.. Moreover, the ability of these materials to establish permanent bonding under physiological conditions has yet to be fully realized.

The known toxicity associated with synthetic adhesives has led to investigations towards the development of biologically derived adhesives as bonding materials. Among such adhesives, fibrin based glues have commanded considerable attention. (See, e.g., Epstein, G. H. et al. *Ann. Otol. Rhinol. Laryngol.* 95: 40–45 (1986); Kram, H. B. et al. *Arch. Surg.* 119: 1309–1311 (1984); Scheele, J. et al. *Surgery* 95: 6–12 (January 1984); and Siedentop, K. H. et al. *Laryngoscope* 93: 1310–1313 (1983) for general discussion of fibrin adhesives). Commercial fibrin tissue adhesives are derived from human plasma and hence pose potential health risks such as adverse immunogenic reactions and transmission of infectious agents, e.g., Hepatitis B virus. Moreover, the bond strength imparted by such adhesives are relatively weak compared to collagen adhesives (see De Toledo, A. R. et al. *Asso. for Res. in Vision and Ophthalmology*, Annual Meeting Abstract, Vol. 31, 317 (1990). Accordingly, there is a need for safe, effective biologically compatible tissue adhesives for biomedical applications.

Collagen, the major connective tissue protein in animals, possesses numerous characteristics not seen in synthetic polymers. Characteristics of collagen often cited include good compatibility with living tissue, promotion of cell growth, and absorption and assimilation of implantations (Shimizu, R. et al. *Biomat. Med. Dev. Art. Org.*, 5(1): 49–66 (1977)). Various applications of this material are being tested, for example, as dialysis membranes of artificial kidney (Sterzel, K. H. et al. *Ameri. Soc. Artif. Int. Organs* 17: 293 (1971)), artificial cornea (Rubin, A. L. et al. *Nature* 230: 120 (1971) and U.S. Pat. No. 4,581,030), vitreous body (Dunn, M. et al. *Amer. Soc. Artif. Int. Organs* 17: 421 (1971)), artificial skin and blood vessels (Krajicek, M. et al. *J. Surg. Res.* 4, 290 (1964)), as hemostatic agents (U.S. Pat. No. 4,215,200), soft contact lens (U.S. Pat. Nos. 4,264,155; 4,264,493; 4,349,470; 4,388,428; 4,452,925 and 4,650,616) and in surgery (Chvapil, M. et al. *Int. Rev. Conn. Tiss. Res.* 6: 1–61 (1973)). Natural collagen fibers, however, are basically insoluble in mature tissues because of covalent intermolecular crosslinks that convert collagen into an infinite crosslinked network. Dispersal and solubilization of native collagen can be achieved by treatment with various proteolytic enzymes which disrupt the intermolecular bonds and removes immunogenic non-helical end regions without affecting the basic, rigid triple-helical structure which imparts the desired characteristics of collagen (see U.S. Pat. Nos. 3,934,852; 3,121,049; 3,131,130; 3,314,861; 3,530,037; 3,949,073; 4,233,360 and 4,488,911 for general methods for preparing purified soluble collagen). Subsequent purification of the solubilized collagen can be accomplished by repeated precipitation at high pH or ionic strength, washing and resolubilization. Introduction of covalent crosslinks into the purified soluble collagen is an important aspect in stabilizing and restructuring the material for biomedical use.

Various methods and materials have been proposed for modifying collagen to render it more suitable as biomedical adhesives. (See, e.g., De Toledo, A. R. et al. *Asso. for Res. in Vision and Ophthalmology*, Annual Meeting Abstract, Vol. 31, 317 (1990); Lloyd et al., "Covalent Bonding of Collagen and Acrylic Polymers," *American Chemical Society Symposium on Biomedical and Dental Applications of Polymers*, Polymer Science and Technology, Vol. 14, Plenum Press (Gebelein and Koblitz eds.), New York, 1980, pp. 59–84; Shimizu et al., *Biomat. Med. Dev. Art. Org.*, 5(1): 49–66 (1977); and Shimizu et al., *Biomat. Med. Dev. Art. Org.*, 6(4): 375–391 (1978), for general discussion on collagen and synthetic polymers.) In many instances, the prior modified collagen-based adhesives suffer from various deficiencies which include (1) crosslinking/polymerization reactions that generate exothermic heat, (2) long reaction times, and (3) reactions that are inoperative in the presence of oxygen and physiological pH ranges (Lee M. L. et al. *Adhesion in Biological Systems*, R. S. Manly, ed., Academic Press, New York, 1970, Chap. 17). Moreover, many of the prior modified collagen-based adhesives contain toxic materials, hence rendering it unsuitable for biomedical use (see, for example, Buonocore, M. G. (1970) and U.S. Pat. No. 3,453,222).

To date, there are no safe, efficacious adhesives for medical use with soft tissue. Collagen-based adhesives with appropriate adhesive strength would have enormous utility in many medical applications, particularly involving soft tissues. Such adhesives could be used to seal incisions following cataract removal and to attach epikeratophakic grafts to corneal tissue, etc. Marketing research has indicated that there are over 8 million surgical procedures that could use a safe, effective biological adhesive.

SUMMARY OF THE INVENTION

The present inventors have discovered that a biologically compatible, collagenous reaction product with sealant and adhesive properties can be formed using chemically modified collagen. Modification of pure, soluble or partially fibrillar collagen monomers with an acylating agent or a sulfonating agent or a combination of the foregoing, renders collagen monomers soluble at physiological conditions. Subsequent polymerization of the chemically modified monomers produces a polymerized collagen composition with adhesive and sealant properties. The polymerization reaction may be initiated with an appropriate polymerizion initiator such as a chemical oxidant, ultraviolet irradiation, a suitable oxidative enzyme or atmospheric oxygen.

Accordingly, it is an object of the present invention to provide polymerized chemically modified collagen compositions as a safe, effective biological adhesives with appropriate adhesive strength for biomedical applications, particularly involving soft tissues. Such adhesives may be used to seal incisions following cataract removal and to attach epikeratophakic grafts to corneal tissue for correction of refractive errors.

It is another object of the present invention to provide a method to dramatically improve the biostability of collagen formulations as determined by resistance to neutral proteases and to vertebrate collagenase.

It is still another object of the present invention to provide a number of collagenous reaction products, that is, a polymerized biologically compatible collagenous reaction product useful in biomedical applications as adhesives and sealants of soft tissue. The polymerized materials may assume a number of sizes and shapes consistent with their intended biomedical applications, which include use in ophthalmology, plastic surgery, orthopedics and cardiology.

It is a further objective of the present invention to provide a process for derivatization of chemically modified collagen monomers with acrylamide which is then polymerized to produce a polyacrylamide-collagen co-polymer. Such materials may be useful for producing mechanical type adhesives, polymerization occurring after the solutions penetrate tissue.

These and other objects will become more apparent in light of the detailed description which follows.

DETAILED DESCRIPTION OF THE INVENTION

Figure 1A:
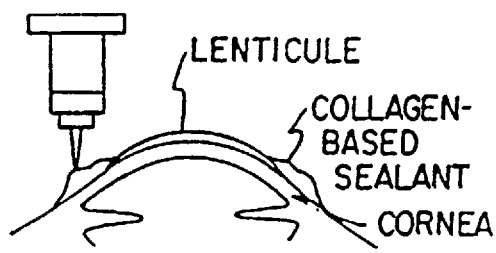
FIGS. 1a–c illustrates the attachment of a lenticule by application of a collagen-based sealant at the periphery of the lenticule in epikeratoplastic procedures.

As employed herein, the term "biologically compatible" refers to collagen modified in accordance with the present invention (i.e., a polymerized collagenous reaction product) which is incorporated or implanted into or placed adjacent to the biological tissue of a subject and more particularly, does not deteriorate appreciably over time or induce an immune response or deleterious tissue reaction after such incorporation or implantation or placement.

The type of collagen useful to form the biologically compatible collagenous reaction product with adhesive properties of this invention is selected from the following groups: purified Type I collagen, Type IV collagen and Type III collagen, intact collagen-rich tissue or a combination of any of the foregoing. Preferred as a collagen starting material is purified Type I collagen. Type I collagen is ubiquitous and readily extracted from animal tissues such as dermis and tendon. Common sources are bovine tendon and hide and rat tail tendon. Extraction from human tissues is difficult. U.S. Pat. No. 4,969,912, "Human Collagen Processing and Autoimplant Use", describes unique methods to disperse and solubilize human tissue.

A variety of collagen solubilization procedures that are well known in the art can be used to prepare soluble collagen solutions useful for the instant invention. Native collagen is liberated from non-collagen connective tissue constituents (lipids, sugars, proteins, etc.) and isolated after subjecting it to proteolytic enzymatic treatment by an enzyme other than collagenase. Suitable proteolytic enzymes include pronase and pepsin. The enzymatic treatment removes the immunogenic non-helical portions of native collagen (telopeptide) and provides a monomeric collagen material which is soluble in dilute acidic aqueous media. A solution containing crude solubilized collagen is then subjected to a series of treatments to purify the soluble atelopeptide collagen from insoluble collagen, protease and non-collagen products resulting from the proteolytic enzymatic procedure. Conventional methods for preparing pure, acid soluble, monomeric collagen solutions by dispersing and solubilizing native collagen are described, for example, in U.S. Pat. Nos. 3,934,852; 3,121,049; 3,131,130; 3,314,861; 3,530,037; 3,949,073; 4,233,360 and 4,488,911. A method for preparing a collagen solution is provided in the examples that follow.

Suitable acylating agents for use in the instant invention include aliphatic, alicyclic and aromatic anhydrides or acid halides. Non-limiting examples of acylating agents include glutaric anhydride, succinic anhydride, lauric anhydride, diglycolic anhydride, methylsuccinic anhydride, methyl glutaric anhydride, dimethyl glutaric anhydride, succinyl chloride, glutaryl chloride, and lauryl chloride. These chemicals are available from Aldrich Chemical Company (Milwaukee, Wis.). Preferred acylating agent for use in the present invention is glutaryl anhydride. An effective amount of an acylating agent is broadly from about 0.5 to 7.5% wt total collagen, preferably from about 1.5 to 5.0% total collagen in solution.

In addition, acylating agents having secondary reactive functionalities within their chemical structure are also useful for modifying collagen monomers. Examples of secondary functionalities include by way of non-limiting examples: epoxy, cyano, halo, alkenyl, and alkynyl. Non-limiting examples of acylating agents bearing secondary functionalities include exo-3,6-epoxy-1,2,3,4-tetrahydrophthalic anhydride, methacrylic anhydride, 3,6-endoxo-3-methylhexahydrophthalic anhydride, and endo-3,6-dimethyl-3,6-endoxohexa hydrophthalic anhydride. Preferred as such acylating agents are exo-3,6-epoxy-1,2,3,4-tetrahydrophthalic anhydride and methacrylic anhydride. Without being bound by theory, the secondary functionalities present in acylating agents can react covalently with amino acid residues under acylation conditions or during polymerization.

Useful sulfonating agents for the preparation of modified collagen monomers of the present invention include aliphatic, alicyclic and aromatic sulfonic acids or sulfonyl halides. Non-limiting examples of sulfonating agents for use in the present invention include anthraquinone-1, 5-disulfonic acid, 2-(chlorosulfonyl)-anthraquinone, 8-hydroxyquinoline sulfonic acid, 2-naphthalene- sulfonyl chloride, beta-styrene sulfonyl chloride and 2-acrylamido-2-methyl-1-propane sulfonic acid. These chemicals are available from Aldrich Chemical Company (Milwaukee, Wis.). Preferred sulfonating agents for preparing the adhesive collagen materials are anthraquinone-1, 5-sulfonic acid and 2-(chlorosulfonyl)-anthraquinone. Such compounds, in non-toxic effective amounts, can be safely employed in collagen-based compounds for medical use as adhesives and sealants. An effective amount of sulfonating agent is broadly from about 0.5 to 20% wt total collagen, preferably from about 1.5 to 7.3 wt % total collagen in solution.

When a combination of an sulfonating agent and acylating agent is used for preparation of modified collagen monomers, the amount of acylating agent and sulfonating agent in total, is preferably from about 1.5 to 7.5% wt of collagen in solution. Excess quantities of chemical modifiers beyond the preferred range may result in a collagen composition that is biologically unstable and sensitive to tissue proteases.

Acylation of collagen is carried out at alkaline pH, for example, in the range from about 7.5 to 10.0, preferably from about 8.5 to 9.5, and more preferably at about pH 9.0. The acylation reaction can be monitored by the decrease in pH. The reaction is complete when pH remains stable. The reaction can also be monitored by removing aliquots and measuring the free amine concentration of precipitated, washed collagen product.

The acylation reaction should be complete in about 5 to about 90 minutes, preferably from about 20 to 40 minutes. The reactions should be carried out at temperatures from about 4° C. to 37° C., preferably from about 4° C. to 25° C.

The reaction can be stopped by adjusting the pH to 12.0 for 2 minutes. This destroys residual, unreacted acylating agent. The modified collagen is then precipitated by reducing the pH using hydrochloric acid, acetic acid, nitric acid, sulfuric acid, or other acid.

The amount of acid must be sufficient to precipitate out the chemically derivatized collagen. Generally precipitation occurs at a pH of between about 3.5 and 6.0, preferably between about 4.0 and 5.0.

The precipitate of reacted collagen which now contains substituent groups reacted with amine groups (primarily epsilon-amino groups), is recovered from the mixture using conventional techniques such as centrifugation or filtration. Centrifugation at about 3,000 to about 15,000 rpm for about 20 to 60 minutes, preferably from about 4,000 to 12,000 for about 20 to 30 minutes provides efficient recovery of the precipitate.

After recovery, the precipitate is washed with deionized water and subsequently dissolved in a physiological solution, e.g., phosphate buffer (0.1M) at pH 7.2. It is often necessary to adjust the pH from about 7.0 to 7.5 by addition of sodium hydroxide solution.

Following dissolution of the precipitate, the solution is generally filtered by conventional filtering means, i.e. a 5 micron filter, and then centrifuged to remove air bubbles. At this point, the resulting solution containing chemically modified collagen monomers exhibits a viscous consistency and varying degrees of transparency and clarity depending on the extent of acylation and on the state of solubility of the starting collagen material.

The extent of acylation determines the biological stability of the resultant sealant or adhesive structure. Complete acylation, reaction with all available free amines, produces a collagen composition with maximum amounts of adhesive moieties. However, such a material may not be biologically stable. Complete acylation results in a collagen sealant that rapidly degrades in the presence of neutral proteolytic enzymes, such as trypsin. It has been discovered that the biological stability of resultant sealants and adhesive systems can be manipulated by controlling the extent of acylation. The extent of acylation may be modulated by varying the amount of acylation agent, the pH, the temperature and the time of the reaction. In addition, the method of addition of the acylating agents will affect the reaction. Reactions are generally slower if the acylating agent is added as a solid or powder rather than as a solution.

Biological stability of the polymerized collagen compositions appears to be additionally affected by the solubility characteristics of the starting collagen. Completely soluble collagen generally does not produce a sealant or adhesive that is resistant to neutral proteolytic enzymes. If the starting collagen solution is adjusted to pH 7.0–7.6 and allowed to undergo limited fibrillogenesis at 25° to 37° C. before chemical modification, the final sealant or adhesive complex is resistant to degradation by neutral proteolytic enzymes, such as trypsin.

The chemically modified collagen solution thus obtained is subsequently subjected to polymerization or crosslinking conditions to produce the polymerized collagen composition of the present invention. Polymerization may be carried out using irradiation, e.g., UV, gamma, or fluorescent light. UV irradiation may be accomplished in the short wave length range using a standard 254 nm source or using UV laser sources. With a standard 254 nm source, 4–12 watts, polymerization occurs from 10 to 40 minutes, preferably 20 to 30 minutes, at an exposure distance of from 2.5–10 cm, preferably from 2.5 to 5 cm distance. Excess UV exposure will begin to depolymerize the collagen polymers. Polymerization using gamma irradiation can be done using from 0.5 to 2.5 Mrads. Excess Gamma exposure will also depolymerize collage polymers. Polymerization in the presence of oxygen can be done by adding an initiator to the fluid prior to exposure. Non-limiting examples of initiators include sodium persulfate, sodium thiosulfate, ferrous chloride tetrahydrate, sodium bisulfite and oxidative enzymes such as peroxidase or catechol oxidase. When initiators are employed, polymerization occurs in 30 seconds to 5 minutes, usually from 1 to 3 minutes.

Preferred as a polymerizing agent is UV irradiation. However, the polymerization or crosslinking of the monomeric substituents can be carried out by simply exposing the material to atmospheric oxygen, although the rate of polymerization is appreciably slower than in the case of UV irradiation or chemical agents.

In one embodiment of the present invention, collagen products containing 2-acrylamido-2-methyl-1-propane sulfonic acid may be mixed with N, N-methylene bisacrylamide to produce mechanical sealants and adhesive systems. Addition of initiators such as sodium persulfate or ammonium persulfate, and exposure to fluorescent light rapidly results in polymerization to form polyacrylamide-collagen co-polymers. Collagen products containing methacrylic acid polymerize spontaneously in air. This polymerization can be accelerated under UV irradiation in the absence of oxygen.

In another embodiment of the present invention, the polymerized collagenous reaction products can be made in the form of a sealant film. As described in the examples which follow, such a film is flexible and elastic with the consistency and feel of plastic film,. and yet the film exhibits high biological compatibility. Uses of sealant films include: Prevention of adhesion formation following tendon surgery, (i.e., use as a wrap around tendons), use as a synthetic tympanic membrane, substitute facial tissue and wound dressing component. Additional examples of potential usage of sealant films include:.treatment of corneal abrasions, wound closure, coating of catheters and instruments, use as a material to prevent adhesion formation in tissues other than tendons (e.g., peritoneal cavity).

Also as further embodiments of the present invention, the sealant-and adhesive formulations can be used as systems specific for delivery of numerous drugs, growth factors, and biological compounds. Such materials can be added to the collagen adhesive or sealant to promote cell migration, cell adhesion, and wound healing.

The working examples set forth below are intended illustrate the invention without limiting its scope.

EXAMPLE 1

A. Preparation of Acid Soluble Type I Collagen Solution

Fibrous Type I collagen was prepared from bovine material (calf hide) using the following procedure:

Clean, dehaired split hides were purchased from the Andre Manufacturing Co. (Newark, N.J.) and frozen until ready for use. Approximately 200 g of calf hide was thawed at room temperature and cut into approximately 1 cm$^3$ pieces using a scalpel and tweezers. The weight of the wet tissue was recorded. The calf hide was then placed into 15 liters of 0.5M acetic acid and stirred with a lightening mixer at room temperature for at least one hour. A ten mL solution of 0.5M acetic acid containing 2% w/w (or 3.9 g) pepsin from porcine mucosa (Sigma Chemicals, St. Louis, Mo.) was added to the calf hide solution. This solution was stirred overnight with a lightening mixer at room temperature. An additional ten mL 0.5M acetic acid solution containing 1% w/w (or 1.96 g) pepsin was added to the calf hide mixture. The solution was again stirred overnight with a lightening mixer at room temperature. The dissolved calf hide solution was refrigerated until a uniform temperature of 4° C. was reached, a process that may take overnight. The pH of the solution was adjusted to 9.0 with 10N NaOH to denature pepsin. Stirring was maintained throughout the pH adjustment process with a lightening mixer. As collagen will precipitate out at pH 9.0 when the temperature is above 6° C., ice-cubes may be added directly to maintain the 4° C. temperature. The solution is then refrigerated for at least four hours, then centrifuged at 4° C. for 30 minutes at 9 rpm. The resulting pellet, containing pepsin, was discarded. The supernatant, containing collagen, was subjected to a series of purification steps.

Collagen was precipitated out by addition of solid NaCl to the supernatant to a final concentration of 2.5M. The solution was stirred at room temperature for at least two hours. The collagen precipitate was collected by centrifugation of solution for 30 minutes at 9000 rpm and redissolved in 15 liters of 0.5M acetic acid, a process requiring at least 2 hours. Collagen was reprecipitated out again by addition of solid NaCl to the solution to a final concentration of 0.8M. The solution stirred for at least two hours and the collagen was collected by centrifugation of the solution for 30 minutes at 9000 rpm. This redissolving/precipitation procedure was repeated once more. The final pellet, containing purified collagen, was dissolved in 0.1M acetic acid of sufficient volume to provide approximately 0.3% w/w collagen Type I solution of pH 3.0. The collagen solution was then prefiltered through a 0.3 micron filter and sterilized through a 0.22 micron filter. The collagen solution can now be used in the modification process.

B. Preparation of Anthraquinone Collagen Using 2-(Chlorosulfonyl)-Anthraquinone Pure collagen was prepared as previously described. Following filtration through a 0.2 micron filter, 100 ml of collagen solution was brought to pH 9.0 and reacted with 6.0 mg of 2-(chlorosulfonyl)-anthraquinone and then 6.0 mg of glutaric anhydride. These chemicals were added in solid form while maintaining the pH at 9.0. After 3 hours, the pH was reduced to 4.5 to precipitate the modified collagen. The precipitate was washed three times with deionized water and subsequently dissolved in 0.005M phosphate buffer, pH 7.5, containing 2% glycerol. The pH was adjusted to 7.4 using in sodium hydroxide. The material was slightly cloudy and was filtered through a 5 micron filter. Approximately 50 ul of 20 mg/ml sodium persulfate was added to 5 ml of the collagen and the mixture exposed to 254 nm UV irradiation for 30 seconds. A firm, flexible film was formed. The same material before UV exposure was used to attach two pieces of bovine dermis. Two sections of dermis approximately 1×1 cm were placed in a glass petri dish side by side. Collagen fluid containing sodium persulfate was painted on each dermis section and over the space adjoining the dermis sections. The sections were then exposed to 254 nm UV irradiation at about 3 cm distance from the source. After exposure for about 60 seconds, the dermis sections were joined. The strength of the joint was not measured. However, the dermis sections remained joined after incubation in sterile 0.9% sodium chloride solution for several weeks.

In another experiment, anthraquinone collagen solution alone (without persulfate) was used to join two sections (each 1×1 cm) of dermal tissue. The sections were exposed to 254 nm UV irradiation for two minutes. The dermal sections became joined and were placed in sterile 0.9% sodium chloride solution. The sections remained attached even after several weeks.

C. Preparation of Anthraquinone Collagen Using Anthraquinone-1, 5-Disulfonic Acid Pure, acid soluble collagen was prepared as previously described. Following filtration through a 0.2 um filter, 100 ml of collagen solution was brought to pH 9.0 and reacted with 6.0 mg of anthraquinone-1, 5-disulfonic acid and 6 mg of glutaric anhydride. These chemicals were added in solid form while maintaining the pH at 9.0. After 30 minutes, the pH was reduced to 4.0 to precipitate the modified collagen. The precipitate was washed three times with sterile water and subsequently dissolved in 0.005M phosphate buffer containing 2% glycerol. The pH was adjusted to 7.4 using 1N NaOH. The material was slightly cloudy. A 50 ul aliquot of sodium persulfate (20 mg/ml) was added to the modified collagen and the material exposed to UV irradiation for 30 seconds. A firm, but flexible mass resulted. The same material before UV irradiation was used to attach two sections of bovine corium. Following brief UV irradiation (30 sec.), the sections became bound together. The tear strength was not measured but appeared sufficient to resist substantial force.

EXAMPLE 2

Sealing Synthetic Lenticules in Epikeratophakia

In this example, a 10 ul aliquot of sodium persulfate (20 mg/ml) was added to a solution containing collagen modified with glutaric anhydride alone. The mixture was placed on the surface of an intact, enucleated bovine eye, and allowed to flow over the surface of the eye for about 2 minutes. At that point, the eye was exposed to UV irradiation for 30 seconds. The collagen mixture polymerized into a thin, somewhat flexible film that covered the eye surface.

In another experiment, glutaric modified collagen without sodium persulfate was added to the surface of an intact, enucleated bovine eye. The eye was then placed in an atmospheric chamber, the chamber flushed with nitrogen, and the eye with collagen coating exposed to UV irradiation for 20 minutes. Again, there appeared to be a smooth, very flexible film of collagen covering the eye.

Figure 1B:
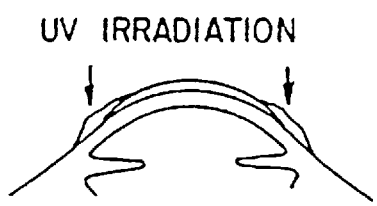
Figure 1C:
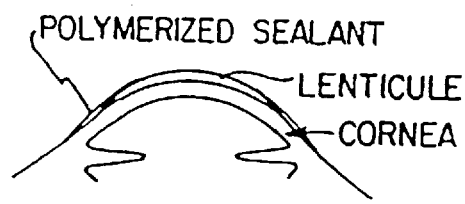
Figure 2A:
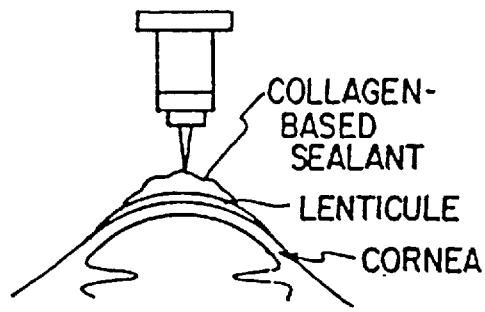
FIGS. 2a–c illustrates the attachment of a lenticule by application of a collagen-based sealant on top of the lenticule in epikeratoplastic procedures. The applied collagen-based sealant coats and seals the lenticule in its entirety.
Figure 2B:
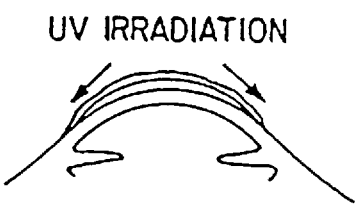
Figure 2C:
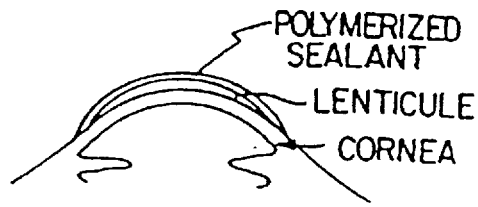

Such a sealant could be useful for attaching a synthetic or natural lenticule in epikeratoplastic procedures. In this case the synthetic or natural lenticule would be positioned on the corneal surface. The collagen sealant would then be placed over the lenticule and adjacent corneal tissue and polymerized in place to seal the lenticule to the adjacent corneal tissue. For example, the collagen-based sealant can be applied on the periphery of the lenticule and adjacent corneal tissue (FIG. 1a), then exposed to UV irradiation (FIG. 1b) to seal the lenticule in place (FIG. 1c). Alternatively, the collagen-based sealant can be placed on top of lenticule (FIG. 2a) which then flows over and coats the surface of the lenticule and adjacent corneal tissue. The coating is then exposed to UV irradiation (FIG. 2b) which seals the lenticule in place (FIG. 2c). Polymerization using UV irradiation must be accomplished in the absence of oxygen. Thus, formulations containing a safe initiator are more practical, eliminating the need to exclude oxygen.

EXAMPLE 3

Resistance to Neutral Protease and Coliagenase and Use for Lenticule Attachment

In this example, pure, soluble collagen was prepared as previously described. Following filtration through a 0.2 um filter, the solution was brought to pH 7.0 and placed in a water bath at 37° C. to initiate collagen fibrillogenesis. After approximately 15 minutes, the solution became cloudy. At this point 100 ml of solution at 2.8 mg/ml collagen was adjusted to pH 9.0 and 7.0 mg of glutaric anhydride was added. The reaction was allowed to continue for another 20 minutes. The pH was then decreased to 4.3 to precipitate the modified collagen. The precipitate was recovered by centrifugation and was washed three times. The final precipitate was very fine and granular. This was dissolved in phosphate buffer and adjusted to pH 7.0–7.4. The viscous solution was clear to slightly cloudy. Films were prepared and exposed to UV irradiation for 20 minutes. Samples were then evaluated for resistance to neutral protease (trypsin) and to vertebrate collagenase. These results were compared to standard glutaric collagen (excess glutaric anhydride). Table 1 shows the results from such evaluation.

TABLE 1

RESISTANCE TO NEUTRAL PROTEASE AND COLLAGENASE
RESISTANCE (%), 24–25 HOURS

|  | Buffer | Trypsin | Vertebrate Collagenase |
|---|---|---|---|
| Standard Glutaric | 95 | 30 | 30 |
| Resistant Glutaric | 100 | 87.4 | 94.7 |

The standard glutaric formulation was examined in situ by placing a sample of the material on the surface of a lenticule and then exposing the material to UV irradiation (short wave length) for 20 minutes in a nitrogen atmosphere. The collagen material was formed into a thin solid film which covered the entire lenticule and seemed to provide a continuous tapering attachment to Bowman's membrane. Epithelial cell migration and attachment had started over the collagen film. However, some of the collagen film began to disintegrate before epithelial cell migration was complete. This probably was caused by epithelial cell proteases.

EXAMPLE 4

Adhesive Formulation

Glutaric modified collagen was prepared using the procedures described in Example 3. The modified collagen was redissolved at about 5% concentration in phosphate buffer (0.005M at pH 7.5) containing 2% glycerol. This high concentration material was supplemented with sodium persulfate (100 ul of a 20 mg/ml solution) per 2 ml of redissolved collagen and used to join two sections of light cardboard. The fluid was painted onto the surfaces of the adjoining cardboard and allowed to wet the surfaces. The pieces were then exposed to UV irradiation for 2 minutes. After exposure, a crude measure of bond strength was made be attaching one piece of cardboard to a clamp suspended from a ring stand and attaching weights to the other piece of cardboard. The joint did not break after adding up to 50 grams of weight.

EXAMPLE 5

Epoxy-Collagen Adhesive

A collagen solution was obtained as previously described. After filtration through a 0.2 filter, 300 ml of collagen solution was brought to pH 7.5 and placed in a water bath at 37° C. until fibril formation was initiated. The pH of the solution was then raised to 9.0 and 42 mg of exo-3,6-epoxy-1,2,3,4-tetrahydrophthalic anhydride added in 10 drops of dimethyl formamide. The pH was maintained at 9.0 for 30 minutes. After 30 minutes the pH was dropped to 7.5 and the solution allowed to equilibrate for an additional 30 minutes. The neutral solution was centrifuged at 9,000 rpm for 20 minutes, the supernatant removed and pH adjusted to 4.3 to precipitate the neutral soluble, epoxy-modified collagen. The precipitate was washed three times with sterile water and reconstituted in 0.005M phosphate buffer, pH 8.6, containing 2% sterile-glycerol. The resulting solution was clear, transparent and viscous. One aliquot of about 5 ml was removed and exposed to 254 nm UV light for 5 minutes. The material thickened but did not polymerize to a hard film. Another aliquot of 5 ml was removed and 25 ul of sodium persulfate (20 mg/ml) added. This was also exposed to 254 nm UV irradiation for 2 minutes. The material polymerized to a relatively firm, but flexible film.

The modified collagen was then used to attach two sections of porous paper. The bond was strong and required significant force to separate the two sections. This same material was used to attach two sections of calf skin. UV irradiation in the absence of oxygen, was used as the initiator in place of the sodium persulfate. After 20 minutes, the sections were firmly attached.

In still another case, an aliquot of epoxy-collagen was added to two sections of porous paper and placed in the laminar flow hood for 10 minutes. The material polymerized and dried to a firm and extremely flexible film that bonded the two sections of paper.

EXAMPLE 6

Methacrylic Collagen Adhesive and Testing

In this example, 200 ml of soluble collagen was modified at pH 9.0 with 30 mg of methacrylic anhydride. The reaction continued for 30 minutes after which 10 mg of glutaric anhydride was added and reacted for another 30 minutes. The modified collagen was precipitated by adjusting the pH to 4.5. The precipitate was recovered by centrifugation and washed three times with sterile water. The material was reconstituted in 0.005M phosphate buffer containing 2% glycerol. The solution was clear and viscous. An aliquot was removed and exposed to 254 nm UV irradiation. After 2 minutes, the material had formed a clear, firm film. Another aliquot was removed and placed on a microscope slide. After 30 minutes, the material had polymerized spontaneously to form a clear, firm film. Two sections of alcohol washed calf skin were placed on a microscope slide, and the interface coated with methacrylic collagen. After 16 hours, the sections were firmly attached. This sample was then incubated in sterile buffer at room temperature. After one week, the sections remained firmly attached.

EXAMPLE 7

Human Tissue adhesive Material

In this example, human dermis was dissected from full thickness skin specimen and blended using an OMNI homogenizer with a Macro generator (10 mm). The tissue did not pulverize in buffer or saline. To the tissue was added 5 mg of methacrylic anhydride per 200 mg of tissue. The tissue immediately pulverized to a fine suspension. A second aliquot of methacrylic anhydride was added to further solubilize the tissue. The pulverized tissue was centrifuged to separate the soluble fraction from the dispersed fraction. The modified tissue in the soluble fraction was recovered by adding 3 volumes of 70% ethanol. The collagen immediately formed fibers. These were recovered by centrifugation and dried in a laminar flow hood. The dried material was then reconstituted in 0.005M phosphate buffer, pH 8.5, containing 2% glycerol. The thick solution was slightly cloudy and viscous. This chemically modified tissue (methacrylic) was exposed to 254 nm UV light for 2 minutes to form a strong, flexible film which could potentially be used as an adhesive to bond tissue.

In another experiment, human tissue was treated with glutaric anhydride instead of methacrylic anhydride. Two aliquots of glutaric anhydride (15 mg/200 mg tissue) were used to disperse and solubilize the human tissue. The soluble fraction was isolated and reconstituted in buffer, as above. The viscous material was extremely sticky. One aliquot was placed on a microscope slide cover slip. After drying the droplets could not be removed from the cover slip, even with a razor blade.

What is claimed is:

1. A method of sealing an opening in a tissue comprising: (1) applying to said tissue a polymerizable collagen composition to cover said opening in said tissue; (2) exposing said polymerizable collagen composition to an initiator so as to initiate polymerization of said polymerizable collagen composition, whereby said exposed polymerizable composition forms a seal over the opening in said tissue.

2. The method of claim 1 wherein said opening is an incision.

3. The method of claim 1 wherein said opening is a wound.

4. The method according to claim 3, wherein said polymerizable collagen composition comprises a collagen selected from the group consisting of purified Type I collagen, purified Type III collagen, purified Type IV collagen and collagen rich tissue.

5. The method according to claim 4, wherein the Type I collagen is derived from human tissue or animal tissue.

6. The method according to claim 5, wherein the Type I collagen comprises autogenic human tissue.

7. The method of claim 1 wherein the polymerizable collagen composition is formed by a reaction between a collagen and at least one of an acylating agent and sulfonating agent.

8. The method according to claim 7, wherein the sulfonating agent is selected from the group consisting of anthraquinone-1,5-disulfonic acid, 2-(chlorosulfonyl)-anthraquinone, 2-acrylamido-2-methyl-1-propane sulfonic acid, 8-hydroxyquinoline-5-sulfonic acid, and beta-styrene sulfonyl chloride.

9. The method according to claim 8, wherein the sulfonating agent is 2-(chlorosulfonyl)-anthraquinone or anthraquinone-1,5-disulfonic acid.

10. The method according to claim 7, wherein the acylating agent is selected from the group consisting of glutaric anhydride, succinic anhydride, lauric anhydride, diglycolic anhydride, methyl succinic anhydride, methyl glutaric anhydride, dimethyl glutaric anhydride, exo-3,6-epoxy-1,2,3,4-tetrahydrophthalic anhydride, 3,6-endoxo-3-methyl hexahydrophthalic anhydride, endo-3,6-dimethyl-3,6-endoxohexahydrophthalic anhydride, methacrylic anhydride, succinyl chloride, glutaryl chloride, and lauryl chloride.

11. The method according to claim 10, wherein the acylating agent is glutaric anhydride.

12. The method according to claim 10, wherein the acylating agent is methacrylic anhydride.

13. The method according to claim 10, wherein the acylating agent is exo-3,6-epoxy-1,2,3,4-tetrahydrophthalic anhydride.

14. The method according to claim 1, wherein the initiator is UV irradiation, sodium persulfate, sodium thiosulfate, ferrous chloride tetrahydrate, sodium bisulfite, an oxidative enzyme, or a combination thereof.

15. The method according to claim 14, wherein UV irradiation is used.

16. The method according to claim 14, wherein sodium persulfate is used.

17. The method according to claim 14, wherein the oxidative enzyme is peroxidase or catechol oxidase.

* * * * *